US012358935B2

(12) United States Patent
Zielonka et al.

(10) Patent No.: US 12,358,935 B2
(45) Date of Patent: Jul. 15, 2025

(54) TARGETING REDOX-ACTIVE PYRIDINIUM CATIONS TO MITOCHONDRIA TO INHIBIT PROLIFERATION OF DRUG-RESISTANT CANCER CELLS

(71) Applicants: The Medical College of Wisconsin, Inc., Milwaukee, WI (US); Lodz University of Technology, Lodz (PL)

(72) Inventors: Jacek Michal Zielonka, Wauwatosa, WI (US); Adam Bartlomiej Sikora, Lodz (PL); Balaraman Kalyanaraman, Milwaukee, WI (US)

(73) Assignees: The Medical College of Wisconsin, Inc., Milwaukee, WI (US); Lodz University of Technology, Lodz (PL)

( * ) Notice: Subject to any disclaimer, the term of this patent is extended or adjusted under 35 U.S.C. 154(b) by 896 days.

(21) Appl. No.: 17/289,646

(22) PCT Filed: Nov. 1, 2019

(86) PCT No.: PCT/US2019/059404
§ 371 (c)(1),
(2) Date: Apr. 28, 2021

(87) PCT Pub. No.: WO2020/092910
PCT Pub. Date: May 7, 2020

(65) Prior Publication Data
US 2021/0395280 A1 Dec. 23, 2021

Related U.S. Application Data

(60) Provisional application No. 62/754,488, filed on Nov. 1, 2018.

(51) Int. Cl.
*C07F 9/58* (2006.01)
*A61K 45/06* (2006.01)
*A61P 35/02* (2006.01)

(52) U.S. Cl.
CPC .............. *C07F 9/58* (2013.01); *A61K 45/06* (2013.01); *A61P 35/02* (2018.01)

(58) Field of Classification Search
CPC ............. C07F 9/58; A61P 35/02; A61K 45/06
See application file for complete search history.

(56) References Cited

U.S. PATENT DOCUMENTS

| 5,206,371 A | 4/1993 | Powers |
| 2011/0059922 A1 | 3/2011 | Zarling |
| 2011/0071099 A1 | 3/2011 | Bielawska |
| 2017/0360964 A1 | 12/2017 | Martens |

FOREIGN PATENT DOCUMENTS

| CN | 107216352 A | * | 9/2017 | ................ C07F 9/59 |

OTHER PUBLICATIONS

Wu, S., et al, Design, synthesis and biological evaluation of mitochondria targeting theranostic agents. Chem. Commun., 2014,50, 8919-8922 (Year: 2014).*
Yang, W., et al. Chemical Communications, 2013. 49(33), pp. 3428-3430 (Year: 2013).*
Bindoli A, et al. Thiol chemistry in peroxidase catalysis and redox signaling. Antioxid Redox Signal. 2008;10(9):1549-64.
Cheng G, et al. Mitochondria-targeted analogues of metformin exhibit enhanced antiproliferative and radiosensitizing effects in pancreatic cancer cells. Cancer Research. 2016;76(13):3904-15.
Elbadawy M, et al. Development of an Experimental Model for Analyzing Drug Resistance in Colorectal Cancer. Cancers. 2018;10(6).
Forman HJ, et al. Signaling functions of reactive oxygen species. Biochemistry. 2010;49(5):835-42.
Forman HJ, et al. An overview of mechanisms of redox signaling. J Mol Cell Cardiol. 2014;73:2-9.
Hammond WA, et al. Pharmacologic resistance in colorectal cancer: a review. Therapeutic advances in medical oncology. 2016;8(1):57-84.
International Searching Authority. International Search Report and Written Opinion for application PCT/US2019/059404. Mailed on Feb. 14, 2020. 14 pages.
Siegel RL, et al. Colorectal cancer statistics, 2017. CA: a cancer journal for clinicians. 2017;67(3):177-93.
Sobotta MC, et al. Peroxiredoxin-2 and STAT3 form a redox relay for H2O2 signaling. Nat Chem Biol. 2015;11(1):64-70.
Wieczorkowska M, et al. 1-methyl-3-nitropyridine: An efficient oxidant of NADH in non-enzymatic and enzyme-mediated processes. Free Radical Research. 2003;37(11):1157-62.
Zielonka J, et al. Mitochondria-Targeted Triphenylphosphonium-Based Compounds: Syntheses, Mechanisms of Action, and Therapeutic and Diagnostic Applications. Chem Rev. 2017;117(15):10043-120. PMC5611849.

* cited by examiner

*Primary Examiner* — Joseph K McKane
*Assistant Examiner* — Quincy McKoy
(74) *Attorney, Agent, or Firm* — Quarles & Brady LLP

(57) ABSTRACT

The present invention provides novel mito-pyridinium compounds, prodrugs and the uses thereof for the treatment of cancer, particularly drug resistant cancer.

27 Claims, 12 Drawing Sheets n = 1 - 18
$R_1, R_2, R_3, R_4, R_5$ = -H, -OCH$_3$, -CH$_3$, -CF$_3$, -C(O)NH$_2$, -CN, -C(O)CH$_3$, -NO$_2$

Mito-MeP-C$_{10}$

Mito-NA-C$_{10}$

Mito-CNP-C$_{10}$

Mito-NP-C$_n$
n = 4, 6, 8, 10 n = 1 - 18
$R_1$, $R_2$, $R_3$, $R_4$, $R_5$ = -H, -OCH$_3$, -CH$_3$, -CF$_3$, -C(O)NH$_2$, -CN, -C(O)CH$_3$, -NO$_2$

R' = methyl (MNAH) or ADP-ribose (NADH)

TARGETING REDOX-ACTIVE PYRIDINIUM CATIONS TO MITOCHONDRIA TO INHIBIT PROLIFERATION OF DRUG-RESISTANT CANCER CELLS

CROSS-REFERENCE TO RELATED APPLICATIONS

This application is a national stage application under 35 CFR 371 to International Application No. PCT/US2019/059404 filed on Nov. 1, 2019 which claims priority to U.S. Provisional Application No. 62/754,488 filed on Nov. 1, 2018, the contents of which are incorporated by reference in their entireties.

STATEMENT REGARDING FEDERALLY SPONSORED RESEARCH OR DEVELOPMENT

N/A

BACKGROUND

Colorectal cancer (CRC) is one of the most common type of cancer and the cause of cancer-related deaths in the United States and western countries.[1] In addition to surgery, chemotherapy represents the main first-line treatment option to CRC. It is estimated that 25% of patients are incurable at diagnosis and 50% of patients who undergo surgery will develop metastases.[2] Despite the advances in chemotherapeutic strategies of the last 20 years, the prognosis for CRC patients presenting metastases remains poor, with a 5-year survival rate of 12.5%.[3] The reason for the poor therapeutic outcome is believed to be drug resistance, occurring in 90% of patients with metastatic CRC. Thus, CRC, and particularly its metastases, are the leading cause of mortality due to their resistance to conventional chemotherapy.

Discovering new molecules that can overcome CRC drug resistance is a critical unmet need.

SUMMARY OF THE INVENTION

The present disclosure demonstrates novel mitochondria-targeted redox cycling agents (mito-pyridinium (Mito-Py) compounds) to inhibit bioenergetic function and stimulate oxidative stress in cancer cells, including colon and pancreatic cancer cells, including drug-resistant human cancer cells, leading to inhibition of cell proliferation and induction of cell death.

In one aspect, the disclosure provides a compound of formula I or prodrug thereof:

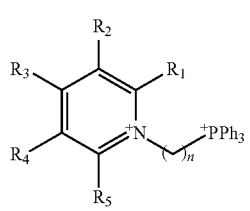

(I)

n = 1-18

$R_1, R_2, R_3, R_4, R_5 =$ —H, —OCH$_3$, —CH$_3$, —CF$_3$, —C(O)NH$_2$, —CN, —C(O)CH$_3$, —NO$_2$ wherein n is an integer selected from 1-18, and $R_1$, $R_2$, $R_3$, $R_4$ and $R_5$ are independently selected from —H, —OCH$_3$, —CH$_3$, —CF$_3$, —C(O)NH$_2$, —CN, —C(O)CH$_3$, and —NO$_2$.

In another aspect, the disclosure provides a method of stimulating superoxide production within a cell, the method comprising: contacting the cancer cell with the compound described herein in an amount effective to inhibit cancer cell growth or proliferation.

In another aspect, the disclosure provides a method of inhibiting cancer cell growth or proliferation, the method comprising contacting the cancer cell with the compound described herein in an amount effective to inhibit cancer cell growth or proliferation.

In yet another aspect, the disclosure provides a method of treating cancer in a subject, the method comprising administering a therapeutically effective amount of the compound described herein in order to treat the cancer. In some examples, the cancer is drug-resistant cancer.

Figure 1:
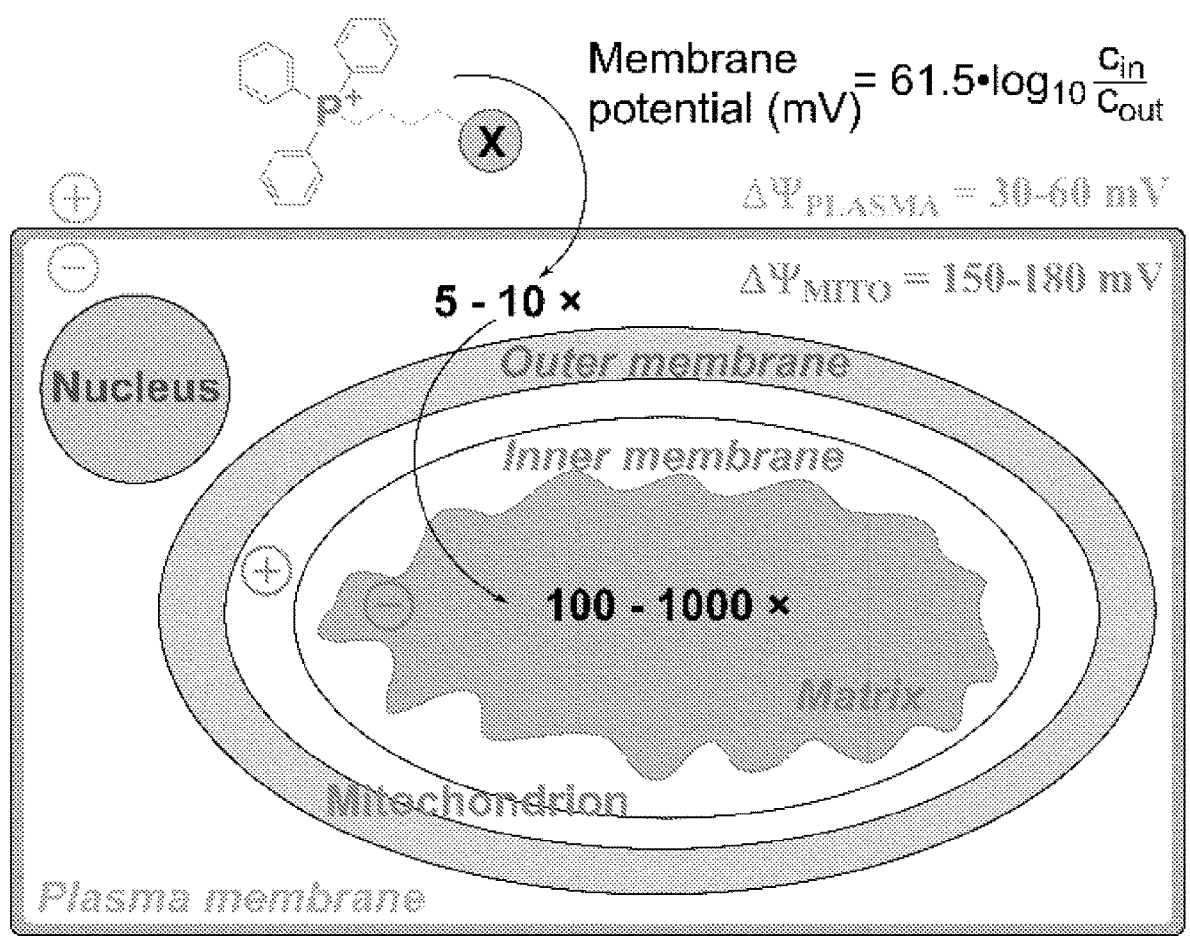
FIG. 1. Membrane potential-dependent cellular and mitochondrial uptake of TPP$^+$-conjugated agents.

The foregoing and other aspects and advantages of the invention will appear from the following description. In the description, reference is made to the accompanying drawings which form a part hereof, and in which there are shown, by way of illustration, preferred embodiments of the invention. Such embodiments do not necessarily represent the full scope of the invention, however, and reference is made therefore to the claims and herein for interpreting the scope of the invention.

DETAILED DESCRIPTION OF THE INVENTION

Before the present materials and methods are described, it is understood that this invention is not limited to the particular methodology, protocols, materials, and reagents described, as these may vary. It is also to be understood that the terminology used herein is for describing particular embodiments only, and is not intended to limit the scope of the present invention that will be limited only by the appended claims.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, cell lines, vectors, animals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

The present disclosure demonstrates novel mitochondria-targeted redox cycling agents (i.e. mito-pyridinium compounds and prodrugs described herein) to inhibit bioenergetic function and stimulate oxidative stress in cancer cells, for example, but not limited to, colon cancer cells or pancreatic cancer cells, including drug-resistant human cancer cells, leading to inhibition of cell proliferation and induction of cell death. As demonstrated in the examples below, the mito-pyridinium compounds and prodrugs synthesized are more potent analogs of simple pyridinium cations. These mito-pyridinium compounds described herein may be used for treatment of cancer, including colon cancer and pancreatic cancer, particularly drug-resistant cancer.

In one embodiment, the present disclosure provides novel mito-pyridinium compounds and prodrugs modified to selectively and synergistically inhibit cancer cell proliferation and progression. Specifically, the inventors have shown that attaching a positively-charged TPP$^+$ moiety to redox active pyridinium compounds induce superoxide production in cancer cells, including colon cancer cells and pancreatic cancer cells. The presence of two positive charges on these molecules is believed to play a role in their action.

The mito-pyridinium compounds of the present invention were observed to be specifically taken up by cancer cells, the extent of uptake was affected by both the substituent in the pyridinium ring (FIG. 4a) and the length of the alkyl linker. The compounds described herein provide anti-proliferative and cytotoxic effects on cancer cells.

The present disclosure provides compounds (i.e. mito-pyridinium compound) of formula I or prodrug thereof:

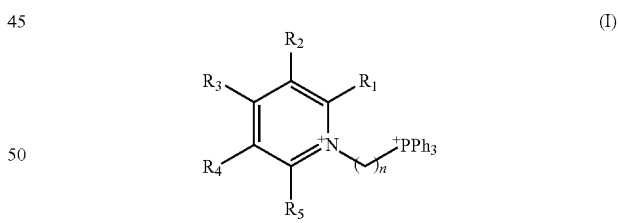

(I)

n = 1-18

$R_1, R_2, R_3, R_4, R_5 = $ —H, —OCH$_3$, —CH$_3$, —CF$_3$,
—C(O)NH$_2$, —CN, —C(O)CH$_3$, —NO$_2$ wherein n is an integer selected from 1-18, and $R_1$, $R_2$, $R_3$, $R_4$ and $R_5$ are independently selected from —H, —OCH$_3$, —CH$_3$, —CF$_3$, —C(O)NH$_2$, —CN, —C(O)CH$_3$, and —NO$_2$. In one example, then is an integer from 4-10. In a preferred embodiment, n is an integer from 8-10 or higher.

In one embodiment, $R_2$ is —CH$_3$, and $R_1$, $R_3$, $R_4$ and $R_5$ are —H in formula I. In a preferred example, n is from 8-10 or higher. For example, the mito-pyridinium is Mito-MeP-C$_{10}$

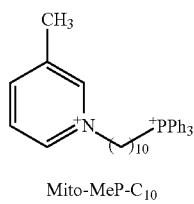

Mito-MeP-C$_{10}$

In another embodiment, R$_2$ is —C(O)NH$_2$ and R$_1$, R$_3$, R$_4$ and R$_5$ are —H in formula I. In a preferred example, n is from 8-10 or higher. For example, the compound is Mito-NA-C$_{10}$

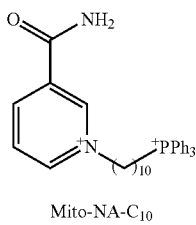

Mito-NA-C$_{10}$

In another embodiment, R$_2$ is —CN and R$_1$, R$_3$, R$_4$ and R$_5$ are —H in formula I. In a preferred example, n is from 8-10 or higher. For example, the compound is Mito-CNP-C$_{10}$.

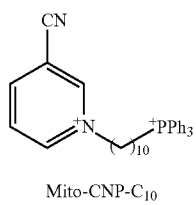

Mito-CNP-C$_{10}$

In another embodiment, R$_2$ is —NO$_2$ and R$_1$, R$_3$, R$_4$ and R$_5$ are —H in formula I. In some embodiments, when R$_2$ is —NO$_2$, and R$_1$, R$_3$, R$_4$ and R$_5$ are —H in formula I, and n is 4, 6, 8 or 10. Preferably, n is 8-10 or higher.

For example, the compound of Mito-NP-Cn

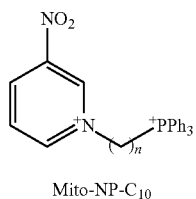

Mito-NP-C$_{10}$ n = 4, 6, 8, 10 wherein n is an integer from 1-10, e.g., 4, 6, 8, 10.

Suitably, in some embodiments, the compound of formula I is Mito-NP-C$_4$, Mito-NP-C$_6$, Mito-NP-C$_8$, or Mito-NP-C$_{10}$.

In another embodiment, the compound is a prodrug. A prodrug is a biologically inactive or less active compound that once administered is metabolized in the body to produce the pharmaceutically active compound. In one example, the compound is a prodrug of formula:

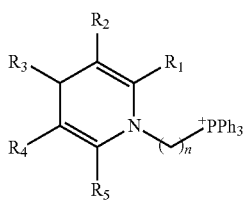

wherein n is an integer selected from 1-18, and R$_1$, R$_2$, R$_3$, R$_4$ and R$_5$ are independently selected from —H, —OCH$_3$, —CH$_3$, —CF$_3$, —C(O)NH$_2$, —CN, —C(O)CH$_3$, and —NO$_2$.

In one example, the prodrug is:

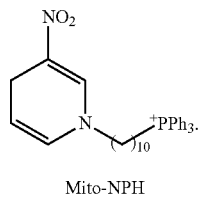

Mito-NPH

Linking pyridinium to triphenylphosphonium (TPP) (mito-pyridinium) increased the level of accumulation of the compound within mitochondria within cells. These mito-pyridinium compounds induced surprising levels of superoxide formation within cancer cells. Superoxide radical anion is the primary form of reactive oxygen species (ROS), which can be converted into other forms of ROS, which can induce redox signaling as well as oxidative damage to cellular components that results in cell death. In addition, similar to other TPP$^+$-linked chemical agents, mito-pyridinium compounds inhibit mitochondrial respiration in cancer cells. This superoxide production leading to alteration of cellular redox status and inhibition of mitochondrial bioenergetic function within cancer cells led to cancer cell growth inhibition and cancer cell death.

Because of the presence of a positive charge on both the pyridinium and TPP$^+$ moieties, the synthesized compounds carry two positive charges. The efficiency of superoxide production by the synthesized compounds is significantly higher than by any other mitochondria-targeted compound reported to date. The compounds exhibit a double mechanism of action, including inhibition of mitochondrial respiration and redox cycling, resulting in oxidation of mitochondrial peroxiredoxin-3, but not cytosolic peroxiredoxin-1, and depletion of cellular ATP level.

Thus present disclosure demonstrates novel mito-pyridinium compounds to inhibit bioenergetic function and stimulate oxidative stress in cancer cells, including colon cancer cells and drug-resistant human colon cancer cells. These compounds lead to inhibition of cancer cell proliferation and induction of cancer cell death. As demonstrated in the examples below, the mito-pyridinium compounds synthesized are more potent analogs of simple pyridinium cations.

In one embodiment, the disclosure provides a method of stimulating superoxide production within a cancer cell, the method comprising contacting the cancer cell with one or more mito-pyridinium compound or prodrug described herein in an amount effective to stimulate superoxide production within the cell.

In another embodiment, the disclosure provides a method of inhibiting cancer cell growth or proliferation, the method comprising contacting the cancer cell with one or more mito-pyridinium compounds or prodrug thereof described herein in an amount effective to inhibit cancer cell growth or proliferation.

The term "contacting" or "exposing," as used herein refers to bringing the disclosed agent or composition and a cancer cell together in such a manner that the agent(s) and/or composition affect the activity of the cancer cell to reduce or inhibit the cancer cell proliferation or growth either directly; i.e., by interacting with the cell itself, or indirectly; i.e., by interacting with another molecule, co-factor, factor, or protein that results in the effect on the cell.

The cancer cell may be in vitro or in vivo. In preferred embodiments, the cancer cell is in vivo within a subject. Suitable cancers that can be treated using the compounds and compositions described herein include, but are not limited to, for example, colon cancer, rectum cancer, pancreas cancer, prostate cancer, lung and bronchus cancer, breast cancer, brain cancer, liver cancer, oral cancer, bladder cancer, stomach cancer, leukemia, among others. In preferred embodiments, the cancer cell is colon cancer or pancreatic cancer and in some examples, drug-resistant colon cancer. These include colon cancer cells with the innate or acquired resistance to 5-fluorouracil or oxaliplatin.

The present invention provides, in some embodiments, a method of treating cancer in a subject, preferably colon or pancreatic cancer, the method comprising administering a therapeutically effective amount of the mito-pyridinium compounds described herein in order to treat the cancer (e.g. colon cancer or pancreatic cancer). In some embodiments, the cancer is drug resistant cancer, for example drug resistant colon cancer.

For purposes of the present invention, "treating" or "treatment" describes the management and care of a subject for the purpose of combating the disease, condition, or disorder. Treating includes the administration of the mito-pyridinium compounds or compositions comprising the mito-pyridinium compounds of present invention to prevent the onset of the symptoms or complications associated with cancer, alleviating the symptoms or complications of cancer, or eliminating the cancer. Treating also encompasses therapeutic and palliative treatment.

The term "treating" can be characterized by one or more of the following: (a) the reducing, slowing or inhibiting the growth or proliferation of cancer cells or tumor cells (e.g., cancers or tumors), including reducing, slowing or inhibiting the growth or proliferation of cancer cells; (b) preventing the further growth or proliferation of cancer cells, for example, colon cancer cells; (c) reducing or preventing the metastasis of cancer cells within a patient, (d) killing or inducing apoptosis of cancer cells, and (d) reducing or ameliorating at least one symptom of cancer. Symptoms of cancer, particularly colon cancer are known in the art and include, but are not limited to, for example, a change in your bowel habits, diarrhea, constipation, a change in the consistency of your stool that lasts longer than four weeks, rectal bleeding, blood in your stool, persistent abdominal discomfort, cramps, gas or pain, feeling that your bowel doesn't empty completely, weakness or fatigue, or unexplained weight loss, among others. Symptoms of other cancers contemplated to be treated by the compounds herein are readily known and ascertainable by one skilled in the relevant art.

In some embodiments, the optimum effective amounts can be readily determined by one of ordinary skill in the art using routine experimentation.

In one embodiment, the term treating is characterized by a reduction in the number of cancer cells in the subject, for example, reduction in the number of colon cancer cells or pancreatic cells in a subject.

As used herein "subject" or "patient" refers to mammals and non-mammals. "Mammals" means any member of the class Mammalia including, but not limited to, humans, non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. The term "subject" does not denote a particular age or sex. In one specific embodiment, a subject is a mammal, preferably a human. In one specific embodiment, the subject is a human with cancer, in some preferred embodiments, the subject is a human having drug-resistant cancer. In one example, the subject has colon cancer, for example, drug resistant colon cancer. In another example, the subject has pancreatic cancer, for example, drug resistant pancreatic cancer.

In some embodiments, the mito-pyridinium compounds exhibit antitumor activity in normal and drug-resistant cancer, including, but not limited to, for example, normal or drug-resistant colon cancer, rectum cancer, pancreas cancer, prostate cancer, lung and bronchus cancer, breast cancer, brain cancer, liver cancer, oral cancer, bladder cancer, stomach cancer, leukemia, among others.

In some embodiments, the compounds may be used alone, in combination with standard of care, for example, chemotherapy, standard-of-care drugs, surgery or radiation. In some embodiments, it is the combination that results in killing of cancer cells, including drug-resistant cancer cells, without significant side effects at the therapeutic doses. Examples of the standard-of-care drugs include 5-fluorouracil, oxaliplatin, regorafenib and bevacizumab. In some examples, the compounds may be used in combination with an immunotherapy which is the standard of care drug. Suitable immunotherapies that may be used with the compounds described herein include, for example, but not limited to, monoclonal antibodies, CAR T-cell therapy, immune checkpoint inhibitors, cancer vaccines, interferons (e.g., INF-alfa), thalidomide, lenalidomide, pomalidomide, imiquimod, cytokines, adjuvants, among others. The type of immunotherapy that is used may depend on the type of cancer being treated and can be determined by one skilled in the art.

In one embodiment, the cancer cell is present in a subject having cancer, for example, colon or pancreatic cancer, wherein the subject has been previously treated with chemotherapy or drug therapy (including but not limited to immunotherapy), and the cancer has been resistant to said therapy. In one example, the cancer is colon cancer. In another embodiment, the cancer cell is pancreatic cancer in a subject.

The terms "cancer," "tumor" or "malignancy" are used throughout this description interchangeably and refer to the diseases of abnormal cell growth. The present methods are for the treatment and amelioration of cancer, preferably colon cancer.

The terms "metastasis" or "secondary tumor" refer to cancer cells that have spread to a secondary site, e.g., outside of the original primary cancer site. Secondary sites include, but are not limited to, for example, the lymphatic system, skin, distant organs (e.g., liver, stomach, pancreas, brain, etc.) and the like and will differ depending on the site of the primary tumor.

As used herein, the terms "effective treatment" refers to the treatment producing a beneficial effect, e.g., yield a desired therapeutic response without undue adverse side effects such as toxicity, irritation, or allergic response. A beneficial effect can take the form of an improvement over baseline, i.e., an improvement over a measurement or observation made prior to initiation of therapy according to the method. A beneficial effect can also take the form of reducing, inhibiting or preventing further growth of cancer cells, reducing, inhibiting or preventing metastasis of the cancer cells or invasiveness of the cancer cells or metastasis or reducing, alleviating, ameliorating, inhibiting or preventing one or more symptoms of the cancer or metastasis thereof. Such effective treatment may, e.g., reduce patient pain, reduce the size or number of cancer cells, may reduce or prevent metastasis of a cancer cell, or may slow cancer or metastatic cell growth.

The terms "effective amount" or "therapeutically effective amount" refer to an amount sufficient to effect beneficial or desirable biological or clinical results. That result can be reducing, inhibiting or preventing the growth of cancer cells, reducing, inhibiting or preventing metastasis of the cancer cells or invasiveness of the cancer cells or metastasis, or reducing, alleviating, inhibiting or preventing one or more symptoms of the cancer or metastasis thereof, or any other desired alteration of a biological system.

By "ameliorate", "amelioration", "improvement" or the like we mean a detectable improvement or a detectable change consistent with improvement occurs in a subject or in at least a minority of subjects, e.g., in at least about 2%, 5%, 10%, 15%, 20%, 25%, 30%, 40%, 50%, 60%, 70%, 75%, 80%, 85%, 90%, 95%, 98%, 100% or in a range about between any two of these values. Such improvement or change may be observed in treated subjects as compared to subjects not treated with the mito-pyridinium compounds of the present invention, where the untreated subjects have, or are subject to developing, the same or similar disease, condition, symptom or the like. Amelioration of a disease, condition, symptom or assay parameter may be determined subjectively or objectively, e.g., self assessment by a subject(s), by a clinician's assessment or by conducting an appropriate assay or measurement, including, e.g., a quality of life assessment, a slowed progression of a disease(s) or condition(s), a reduced severity of a disease(s) or condition(s), or a suitable assay(s) for the level or activity(ies) of a biomolecule(s), cell(s) or by detection of cell migration within a subject. Amelioration may be transient, prolonged or permanent or it may be variable at relevant times during or after the mito-pyridinium compounds of the present invention is administered to a subject or is used in an assay or other method described herein or a cited reference, e.g., within about 1 hour of the administration or use of the mito-pyridinium compounds of the present invention to about 3, 6, 9 months or more after a subject(s) has received the mito-pyridinium compounds of the present invention.

By "modulation" of, e.g., a symptom, level or biological activity of a molecule, replication of a pathogen, cellular response, cellular activity or the like means that the cell level or activity is detectably increased or decreased. Such increase or decrease may be observed in treated subjects as compared to subjects not treated with the mito-pyridinium compounds of the present invention, where the untreated subjects have, or are subject to developing, the same or similar disease, condition, symptom or the like. Such increases or decreases may be at least about 2%, 5%, 10%, 15%, 20%, 25%, 30%, 40%, 50%, 60%, 70%, 75%, 80%, 85%, 90%, 95%, 98%, 100%, 150%, 200%, 250%, 300%, 400%, 500%, 1000% or more or about within any range about between any two of these values. Modulation may be determined subjectively or objectively, e.g., by the subject's self assessment, by a clinician's assessment or by conducting an appropriate assay or measurement, including, e.g., quality of life assessments or suitable assays for the level or activity of molecules, cells or cell migration within a subject. Modulation may be transient, prolonged or permanent or it may be variable at relevant times during or after the mito-pyridinium compounds of the present invention is administered to a subject or is used in an assay or other method described herein or a cited reference, e.g., within about 1 hour of the administration or use of the mito-pyridinium compounds of the present invention to about 3, 6, 9 months or more after a subject(s) has received the mito-pyridinium compounds of the present invention.

As used herein, the terms "administering" and "administration" refer to any method of providing the treatment to the patient, for example, any method of providing a pharmaceutical preparation to a subject. Such methods are well known to those skilled in the art and include, but are not limited to, oral administration, transdermal administration, administration by parenteral administration, including injectable such as intravenous administration, intra-arterial administration, intramuscular administration, intradermal administration, intrathecal administration and subcutaneous administration, rectal administration, sublingual administration, buccal administration, among others. Administration can be continuous or intermittent. In various aspects, a preparation or combination of compounds can be administered therapeutically; that is, administered to treat an existing disease or condition.

In some embodiments, the present invention provides pharmaceutical compositions comprising the mito-pyridinium compounds of the present invention and at least one pharmaceutically acceptable carrier. The term "pharmaceutically acceptable carrier" refers any carrier, diluent or excipient that is compatible with the other ingredients of the formulation and not deleterious to the recipient. Pharmaceutically acceptable carrier can be selected on the basis of the selected route of administration and standard pharmaceutical practice for the compounds. The active agent may be formulated into dosage forms according to standard practices in the field of pharmaceutical preparations. See Alphonso Gennaro, ed., Remington's Pharmaceutical Sciences, 18th Ed., (1990) Mack Publishing Co., Easton, Pa. Suitable dosage forms may comprise, for example, tablets, capsules, solutions, parenteral solutions, injectable solutions, troches, suppositories, or suspensions.

For oral administration, the active ingredient may be combined with one or more solid inactive ingredients for the preparation of tablets, capsules, pills, powders, granules or other suitable oral dosage forms. For example, the active agent may be combined with at least one excipient such as fillers, binders, humectants, disintegrating agents, solution retarders, absorption accelerators, wetting agents absorbents or lubricating agents.

For parenteral administration, the active agent may be mixed with a suitable carrier or diluent such as water, an oil (e.g., a vegetable oil), ethanol, saline solution (e.g., phosphate buffer saline or saline), aqueous dextrose (glucose) and related sugar solutions, glycerol, or a glycol such as propylene glycol or polyethylene glycol. Stabilizing agents, antioxidant agents and preservatives may also be added. Suitable antioxidant agents include sulfite, ascorbic acid, citric acid and its salts, and sodium EDTA. Suitable preservatives include benzalkonium chloride, methyl- or propylparaben, and chlorbutanol. The composition for parenteral administration may take the form of an aqueous or nonaqueous solution, dispersion, suspension or emulsion.

The pharmaceutical composition is preferably in unit dosage form. In such form the preparation is divided into unit doses containing appropriate quantities of the active component.

Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician.

Kits. In another embodiment, the present invention provides a kit comprising a pharmaceutical composition comprising the mito-pyridinium compounds of the present invention and instructional material. By "instructional material" we mean a publication, a recording, a diagram, or any other medium of expression which is used to communicate the usefulness of the pharmaceutical composition of the invention for one of the purposes set forth herein in a subject. The instructional material can also, for example, describe an appropriate dose of the pharmaceutical composition of the invention. The instructional material of the kit of the invention can, for example, be affixed to a container which contains a pharmaceutical composition of the invention or be shipped together with a container which contains the pharmaceutical composition. Alternatively, the instructional material can be shipped separately from the container with the intention that the instructional material and the pharmaceutical composition be used cooperatively by the recipient.

It should be apparent to those skilled in the art that many additional modifications beside those already described are possible without departing from the inventive concepts. Variations of the term "comprising" should be interpreted as referring to elements, components, or steps in a non-exclusive manner, so the referenced elements, components, or steps may be combined with other elements, components, or steps that are not expressly referenced. Embodiments referenced as "comprising" certain elements are also contemplated as "consisting essentially of" and "consisting of" those elements. The term "consisting essentially of" and "consisting of" should be interpreted in line with the MPEP and relevant Federal Circuit interpretation. The transitional phrase "consisting essentially of" limits the scope of a claim to the specified materials or steps "and those that do not materially affect the basic and novel characteristic(s)" of the claimed invention. "Consisting of" is a closed term that excludes any element, step or ingredient not specified in the claim.

The invention will be more fully understood upon consideration of the following non-limiting examples.

EXAMPLES

Example 1

This Example demonstrates new molecules that can overcome CRC drug resistance. Mitochondria-targeted redox cycling agents are able to inhibit bioenergetic function and stimulate oxidative stress in drug-resistant human colon cancer cells, leading to inhibition of cell proliferation and induction of cell death.

Despite the reliance of cancer cells on glycolytic metabolism, in many cancer types mitochondria are functional and important for cell survival and proliferation. This led to development of novel anticancer strategies, based on targeting cancer cell mitochondrial function. One of such approach is based on targeting bioactive compounds to mitochondria by conjugation to the triphenylphosphonium cationic moiety ($TPP^+$) using alkyl linkers (FIG. 1).[4] It has been shown that $TPP^+$-conjugated compound accumulate selectively in cancer cells in vitro and in tumor tissues in vivo. Several such compounds were shown to inhibit mitochondrial respiration with concomitant stimulation of mitochondrial oxidants. Inhibition of mitochondrial respiration, with concomitant decrease in cellular ATP was proposed to prevent the efflux of the compounds via the drug resistance proteins.

Figure 2:
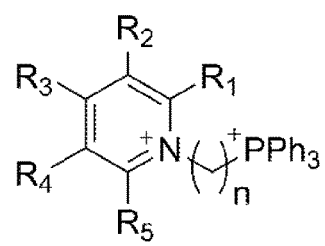
FIG. 2. Proposed structures of mitochondria-targeted pyridinium cations.

We hypothesized that concomitant targeting cancer cell mitochondrial bioenergetics and redox status by conjugation of the $TPP^+$ moiety to a redox active pyridinium cations would provide a new way to efficiently stop proliferation of drug-resistant cancer cells. We designed and synthesized novel redox active pyridinium compounds linked to the $TPP^+$ moiety (FIG. 2), as efficient redox cycling agents, inducing superoxide production in colon cancer cells. Because of the presence of a positive charge on both the pyridinium and $TPP^+$ moieties, the synthesized compounds carry two positive charges.

Figure 3:
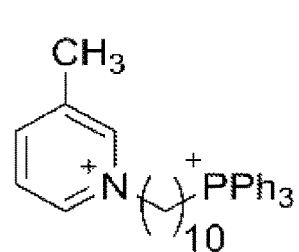
FIG. 3. Chemical structures of the synthesized compounds.
Figure 3:
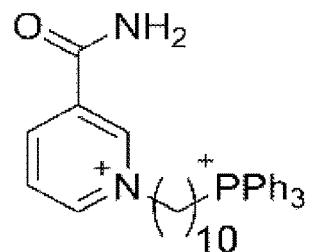
Figure 3:
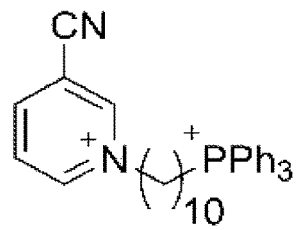
Figure 3:
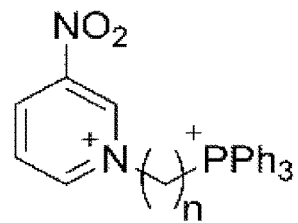

Synthesis of mitochondria-targeted pyridinium cations. We have successfully synthesized a series of pyridinium compounds carrying different substituents at position 3 of the pyridinium ring and linked to the $TPP^+$ moiety via a 10-carbon chain link (FIG. 3). For the pyridinium cation carrying the nitro substituents (exhibiting the most positive reduction potential) we have also synthesized homologs of different linker chain length. The structures of the synthesized compounds have been confirmed by HRMS (high-resolution mass spectroscopy) and the purity was determined by HPLC.

Figures 4A, 4B:
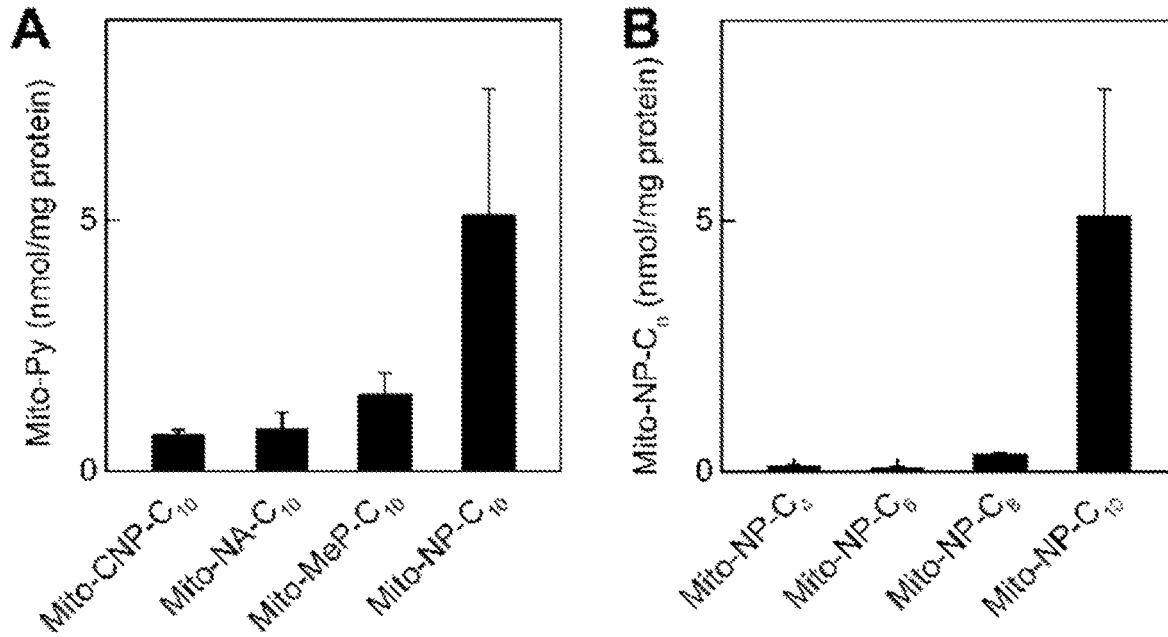
FIGS. 4A-4B. Intracellular uptake of Mito-Py. LS513 colon cancer cells were incubated for 2 h with 50 μM Mito-Py before cell harvesting and compound extraction. (A) Effect of the substituent on the pyridinium ring. (B) Effect of the alkyl linker length in Mito-NP.

Cellular uptake of mitochondria-targeted pyridinium cations. To confirm the cellular accumulation of the synthesized compounds, we have determined their intracellular levels in LS513 colon cancer cells using LC-MS/MS analyses (FIG. 4). We have observed that cellular uptake was affected both by the substituent in the pyridinium ring (FIG. 4A) and by the length of the alkyl linker (FIG. 4B). Importantly, the Mito-NP-$C_{10}$ compound exhibited maximal uptake among the synthesized compounds.

Figures 5A, 5B:
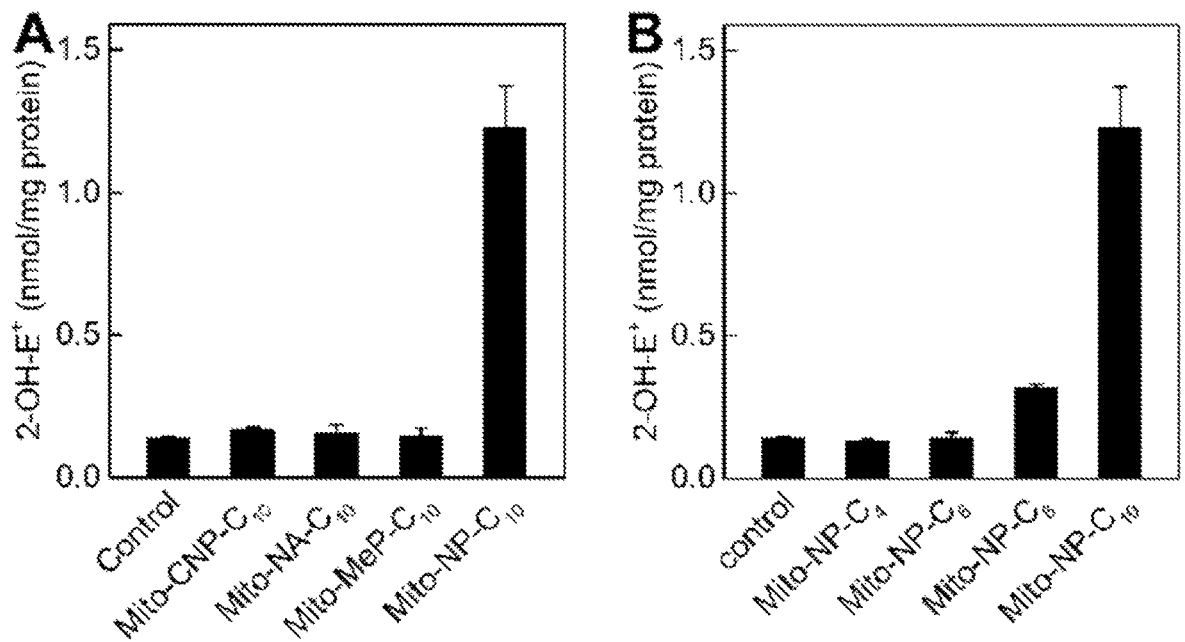
FIGS. 5A-5B. Stimulation of intracellular superoxide of Mito-Py. LS513 colon cancer cells were pre-incubated for 1 h with 50 μM Mito-Py followed by 1-h incubation with the HE probe. 2-OH-E$^+$ is a specific product of the reaction of the probe with superoxide. (A) Effect of the substituent on the pyridinium ring. (B) Effect of the alkyl linker length in Mito-NP.

Induction of superoxide production by mitochondria-targeted pyridinium cations. To unequivocally demonstrate the stimulation of superoxide formation by mitochondria-targeted pyridinium cations (Mito-Py), we used a hydroethidine (HE)-based assay coupled with an HPLC analysis of the superoxide-specific product, 2-hydroxyethidium (2-OH-$E^+$). The data obtained (FIG. 5) indicate that Mito-NP-$C_{10}$ is the most potent inducer of superoxide production, with an efficiency that, to date, has not been observed for any other mitochondria-targeted agents. While the cellular uptake is clearly one of the determinants of superoxide production (FIG. 5B), the redox properties seem to be the major factor affecting the redox cycling properties, as Mito-NP-$C_8$ stimulated superoxide production, while Mito-Py-$C_{10}$ containing groups other than the nitro group on the pyridinium ring failed to induce superoxide formation (FIG. 5B) even though their cellular uptake was higher than that of Mito-NP-$C_8$ (FIG. 4).

Intracellular localization of redox stress. To understand the fate of superoxide induced by Mito-NP-$C_{10}$ and determine the localization of the redox cycling process, we performed redox blotting of peroxiredoxin isoforms 1 and 3

Figures 6A, 6B:
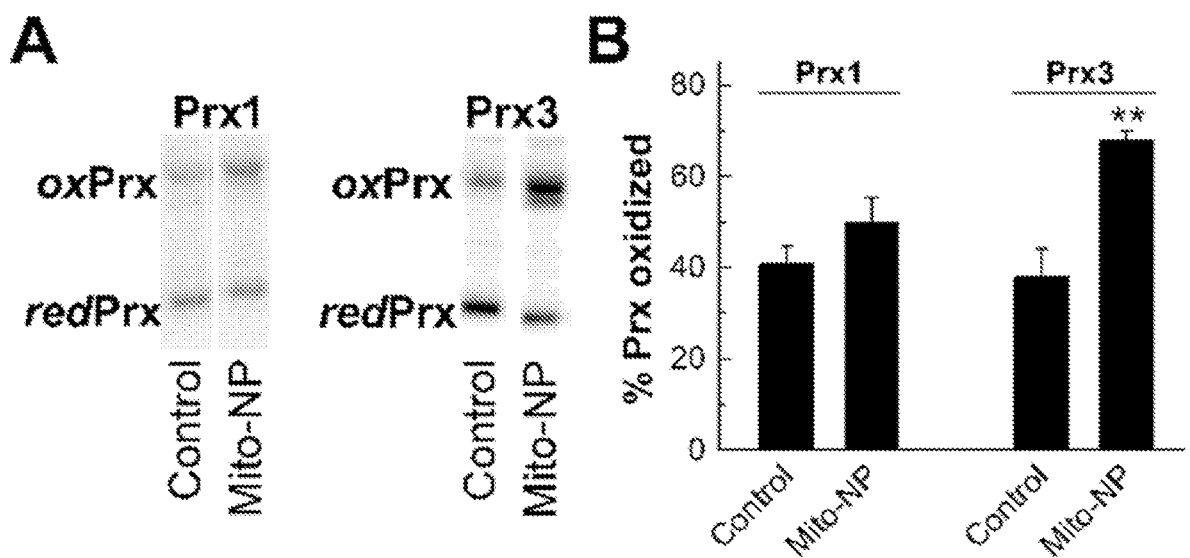
FIG. 6. Effect of Mito-NP-C$_{10}$ (10 μM, 1 h) on the redox status of cytosolic (Prx1) and mitochondrial (Prx3) peroxiredoxins. **p<0.01

(Prx1 and Prx3). Prx proteins have been proposed to act not only as highly efficient antioxidant enzymes but also as mediators of redox signaling.[5-8] We found that treatment of LS513 cells with 10 µM Mito-NP-$C_{10}$ induces significant oxidation of mitochondrial Prx3 but not cytosolic Prx1 (FIG. 6). These data are consistent with the proposed mitochondrial accumulation and site-specific redox cycling by Mito-NP in mitochondria of LS513 colon cancer cells.

Figure 7:
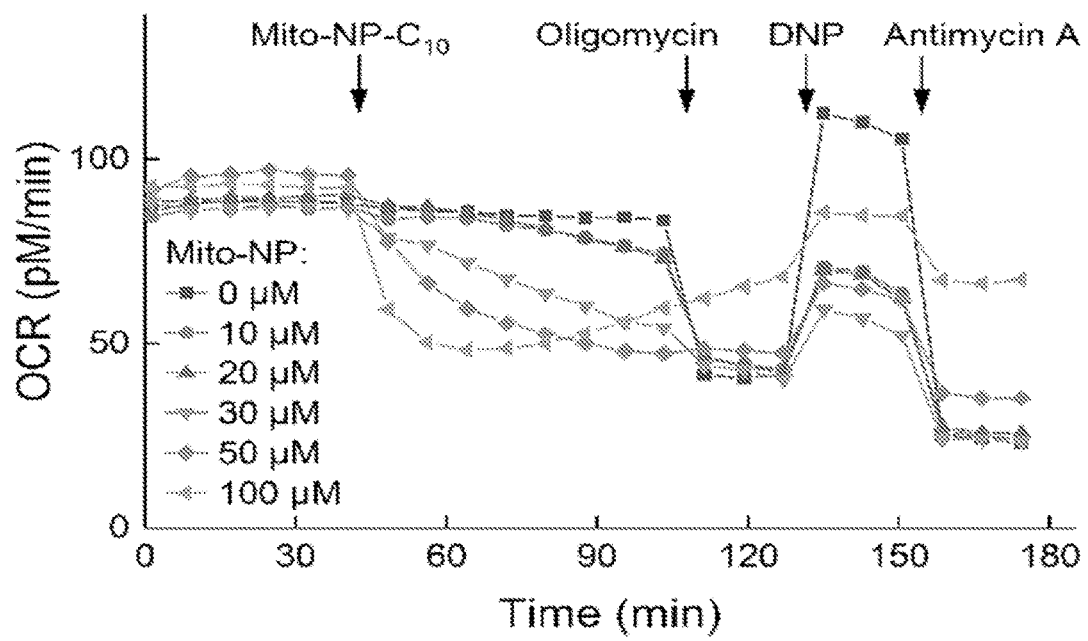
FIG. 7. Effect of Mito-NP-C$_{10}$ (0-100 μM) on the rates of oxygen consumption (OCR) by LS513 colon cancer cells, and on the cell response to mitochondrial stressors: oligomycin (ATP synthase inhibitor), dinitrophenol (DNP, mitochondrial uncoupler) and antimycin A (mitochondrial complex III inhibitor).

Induction of bioenergetic stress. To test the effect of Mito-NP-$C_{10}$ on the bioenergetic function of LS513 cells, we monitored the mitochondrial respiration in response to acute addition of the compound at different doses (FIG. 7). We observed that addition of Mito-NP-$C_{10}$ led to time- and concentration-dependent inhibition in mitochondrial respiration rates, as well as a loss in response to oligomycin (ATP synthase inhibitor), dinitrophenol (DNP, mitochondrial uncoupler) and antimycin A (complex III inhibitor). These data are consistent with inhibition of mitochondrial respiration and ATP synthesis. Interestingly, at 30 and 100 µM concentrations, Mito-NP-$C_{10}$ increased the rates of antimycin A-independent oxygen consumption, suggesting significant stimulation of the production of reactive oxygen species, consistent with the data on superoxide formation (FIG. 5).

Figures 8A, 8B:
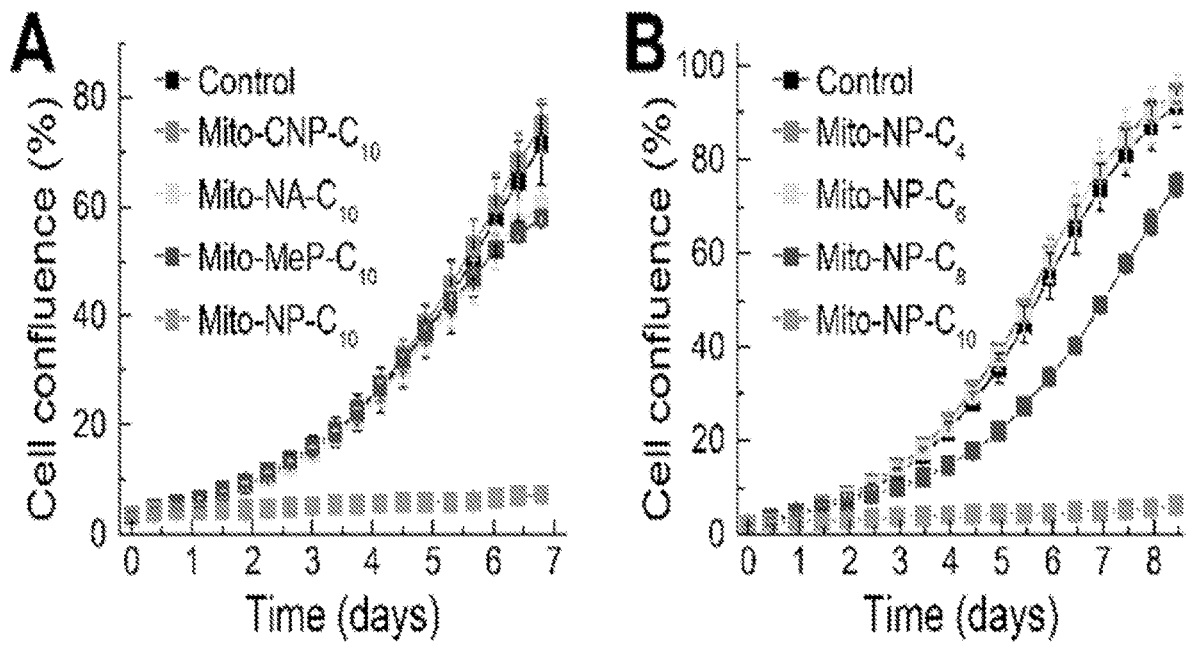
FIG. 8. Effect of Mito-Py compounds (10 μM) on the proliferation of LS513 cells. (A) Effect of the substituent on the pyridinium ring. (B) Effect of the alkyl linker length in Mito-NP.
Figure 9:
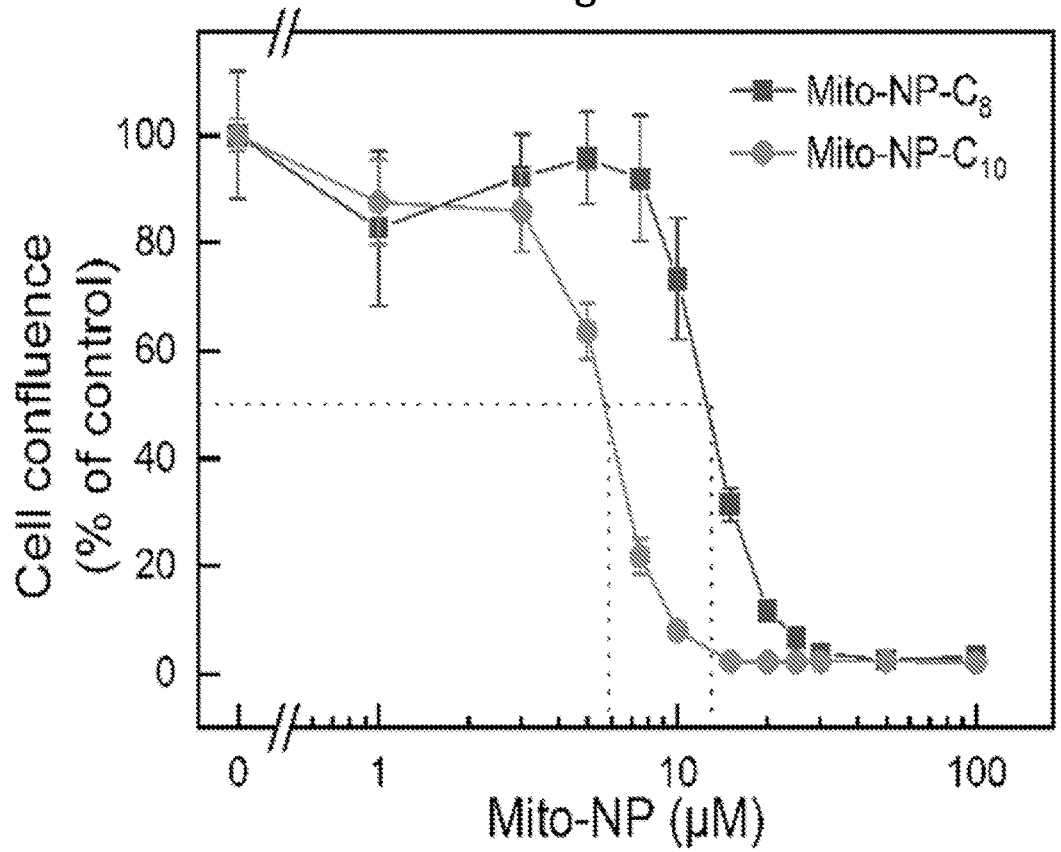
FIG. 9. Effect of concentration of Mito-NP-C$_8$ and Mito-NP-C$_{10}$ on the LS513 cell confluence. Dashed lines correspond to 50% cell confluence.

Antiproliferative effects of mitochondria-targeted pyridinium cations. To test if the mitochondrial redox stress induced by Mito-Py compounds would translate into inhibition of cancer cell proliferation, we compared the effects of Mito-Py of different redox potential and different alkyl linker length on proliferation of LS513 cells. We used the IncuCyte™ Live-Cell Imaging Analyzer that provides real-time cell confluence data (FIG. 8). Among the different substituents present in the pyridinium moiety, only Mito-NP blocked the proliferation of colon cancer cells under the conditions used (FIG. 8A). Moreover, while short alkyl linkers (n=4, 6) did not affect cell proliferation, longer linkers, including n=8 and 10, lead to the inhibition of cell proliferation, with the latter exhibiting much higher efficiency at the concentration tested (FIG. 8B). The concentration dependence allowed us to estimate the $IC_{50}$ values for Mito-NP-$C_8$ and Mito-NP-$C_{10}$ (FIG. 9), which equal to 13 µM and 6 µM, respectively. Clearly, these data well reflect the data on stimulation of superoxide production (FIG. 5) rather than just compound uptake (FIG. 4), suggesting redox cycling activity is an important factor affecting the antiproliferative properties of the compounds. Prolonged (>24 h) incubation of cells with Mito-NP-$C_8$ and Mito-NP-$C_{10}$ results in cell death, as assayed using Sytox Green fluorescent dye (not shown).

Mitochondria-targeted pyridinium cations represent a new class of mitochondria targeted drugs that have a dual mechanism of action in drug resistant cancer cells: inhibition of respiration (bioenergetic signaling) and redox cycling (redox signaling and depletion of intracellular antioxidants). Unlike the $TPP^+$-linked pyridinium cation reported here, most other mitochondria targeted $TPP^+$-conjugated molecules are mono-cations. We believe that this aspect will markedly affect the therapeutic window of this class of compounds.

REFERENCES

1. Siegel R L, Miller K D, Fedewa S A, Ahnen D J, Meester R G S, Barzi A, Jemal A. Colorectal cancer statistics, 2017. C A: a cancer journal for clinicians. 2017; 67(3): 177-93.

2. Elbadawy M, Usui T, Yamawaki H, Sasaki K. Development of an Experimental Model for Analyzing Drug Resistance in Colorectal Cancer. Cancers. 2018; 10(6). PMC6025190

3. Hammond W A, Swaika A, Mody K. Pharmacologic resistance in colorectal cancer: a review. Therapeutic advances in medical oncology. 2016; 8(1):57-84. PMC4699262

4. Zielonka J, Joseph J, Sikora A, Hardy M, Ouari O, Vasquez-Vivar J, Cheng G, Lopez M, Kalyanaraman B. Mitochondria-Targeted Triphenylphosphonium-Based Compounds: Syntheses, Mechanisms of Action, and Therapeutic and Diagnostic Applications. Chem Rev. 2017; 117(15):10043-120. PMC5611849

5. Bindoli A, Fukuto J M, Forman H J. Thiol chemistry in peroxidase catalysis and redox signaling. Antioxid Redox Signal. 2008; 10(9):1549-64. PMC2693905

6. Forman H J, Maiorino M, Ursini F. Signaling functions of reactive oxygen species. Biochemistry. 2010; 49(5):835-42. PMC4226395

7. Forman H J, Ursini F, Maiorino M. An overview of mechanisms of redox signaling. J Mol Cell Cardiol. 2014; 73:2-9. PMC4048798

8. Sobotta M C, Liou W, Stocker S, Talwar D, Oehler M, Ruppert T, Scharf A N, Dick T P. Peroxiredoxin-2 and STAT3 form a redox relay for $H_2O_2$ signaling. Nat Chem Biol. 2015; 11(1):64-70.

Example 2

Figure 13:
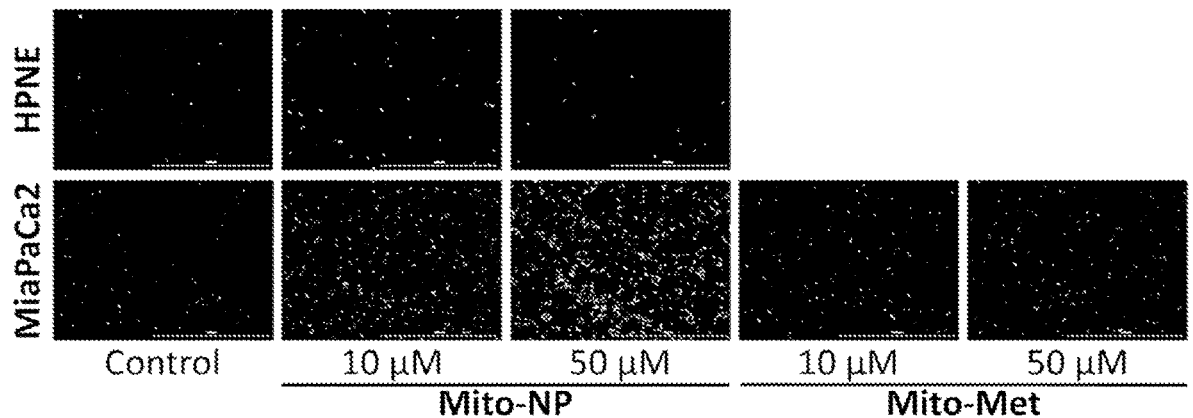
FIG. 13. Cytotoxic effects of Mito-NP against pancreatic cancer (MiaPaCa2) and non-cancer (HPNE) cells, in comparison to mito-metformin (Mito-Met). Cells were stained with Sytox Green dye after 48-h treatment with the compounds to label dead cells.

1. Antiproliferative and cytotoxic effects in pancreatic cancer cells. We have tested the effect of Mito-NP on human (MiaPaCa2 and Panc1) and mouse (FC1242) pancreatic ductal adenocarcinoma (PDAC) cells and observed concentration-dependent inhibition of the cell growth, with the determined $IC_{50}$ values of 2.7±0.2, 2.8±0.3, and 3.1±0.1 µM for MiaPaCa2, Panc1, and FC1242 cells, respectively (FIG. 11A). The control compounds lacking the mitochondria-targeting $TPP^+$ moiety, methyl- and decyl-nitropyridinium cations showed lower antiproliferative properties than Mito-NP (FIG. 11B). These observations suggest the unique ability of Mito-NP to accumulate in cancer cells mitochondria, resulting in inhibition of cancer cell proliferation. To determine the cytotoxic potency of Mito-NP, we used Sytox Green fluorescent marker, which accumulates in dead cells and increases its fluorescence yield upon binding DNA. As shown in FIG. 13, Mito-NP dose-dependently induced death of MiaPaCa2 cells. To determine if redox cycling activity of Mito-NP was important for its cytotoxic effects, we also tested mito-metformin (Mito-Met), which we previously reported to potently inhibit pancreatic cancer cell proliferation, due to inhibition of mitochondrial complex I. We observed that Mito-NP was a significantly stronger inducer of MiaPaCa2 cell death than Mito-Met (FIG. 13), demonstrating the susceptibility of pancreatic cancer cells to dual induction of bioenergetic and redox stress. No induction of cell death was observed in non-tumorigenic human pancreatic duct cell line (HPNE) upon Mito-NP treatment (FIG. 13).

Figure 14:
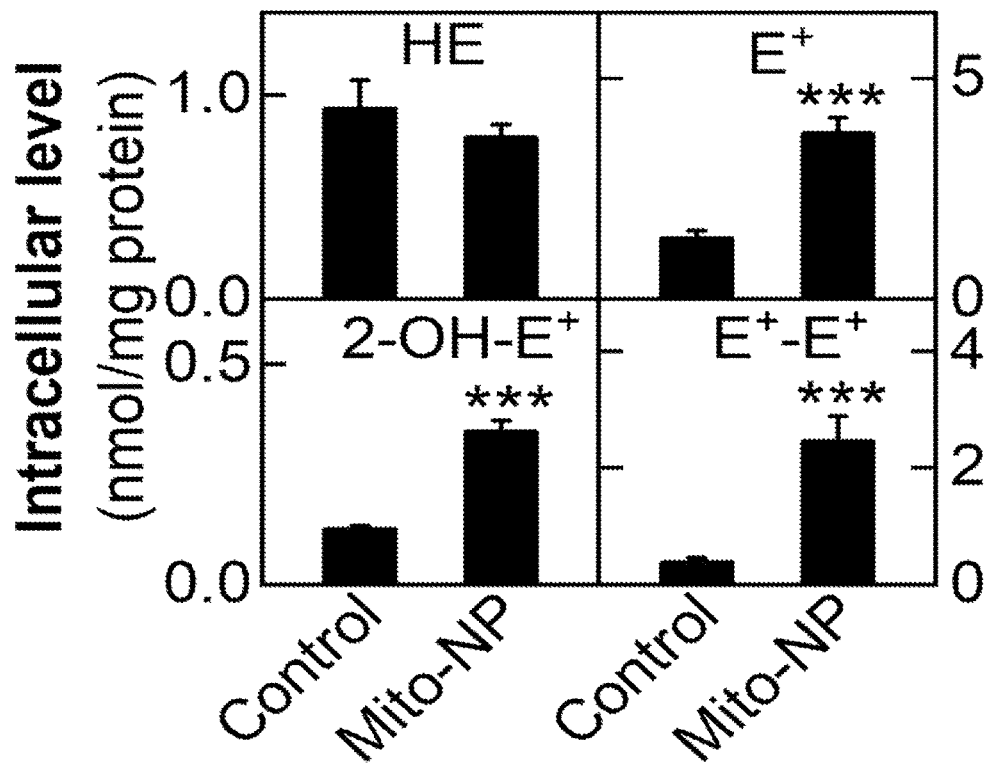
FIG. 14. Stimulation of cellular oxidants by Mito-NP in pancreatic cancer cells. Profiles of HE oxidation products in MiaPaCa2 cells treated with Mito-NP (10 μM, 4 h).

2. Induction of the Redox Stress in Pancreatic Cancer Cells
  2.1. Generation of $O_2.^-$ and other oxidants. We have tested the ability of Mito-NP to stimulate $O_2.^-$ production in MiaPaCa2 cells using HE probe with HPLC-based profiling of the oxidation products.[32] Treatment with Mito-NP led to a significant increase in the production of $O_2.^-$, as evidenced by an increased level of the $O_2.^-$-specific product, 2-hydroxyethidium (2-OH-$E^+$, FIG. 14). An increased level of other oxidation products indicates the formation of stronger oxidants, including iron-oxo species and/or the hydroxyl radical (OH). We have confirmed the mitochondrial localization of $O_2.^-$ production using Mito-SOX (Mito-HE-$C_6$) probe with HPLC-based detection of, 2-OH-Mito-$E^+$, the $O_2.^-$-specific oxidation product of MitoSOX (not shown).

Figure 15:
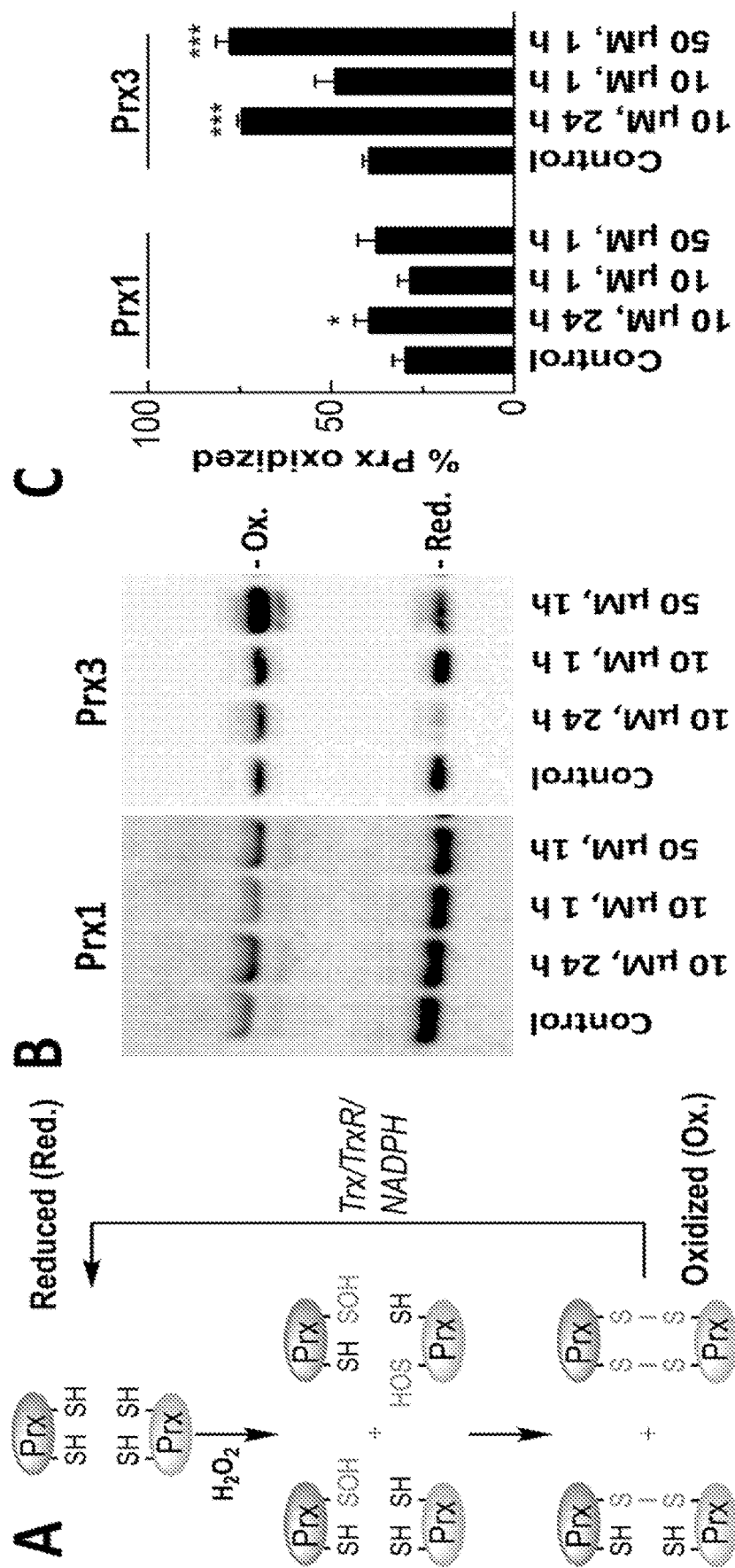
FIG. 15. Effect of Mito-NP on the redox status of cytosolic (Prx1) and mitochondrial (Prx3) peroxiredoxins in MiaPaCa2 cells. *p<0.05, ***p<0.001.

2.2. Prx oxidation. Increased production of $O_2.^-$ results in elevated $H_2O_2$ flux. We tested the effect of Mito-NP on the redox status of cytosolic (Prx1) and mitochondrial (Prx3) peroxiredoxins (FIG. 15A). Peroxiredoxins are the primary targets of cellular $H_2O_2$ and are responsible for removal of up to 90% of mitochondrial $H_2O_2$.[177] It has been shown that peroxiredoxins (Prxs) may serve as the $H_2O_2$ sensors for cellular redox signaling, by oxidizing other proteins via redox relay mechanism.[178,179] We used Prx1 and Prx3 as endogenous, site-specific markers of the redox stress.[180] Mito-NP induced strong oxidation of mitochondrial Prx3, with only modest effect on cytosolic Prx1 (FIG. 15B,C). This indicates that Mito-NP-induced redox stress is predominantly localized in cell mitochondria.

3. Induction of the Bioenergetic Stress in Pancreatic Cancer Cells

Figure 16:
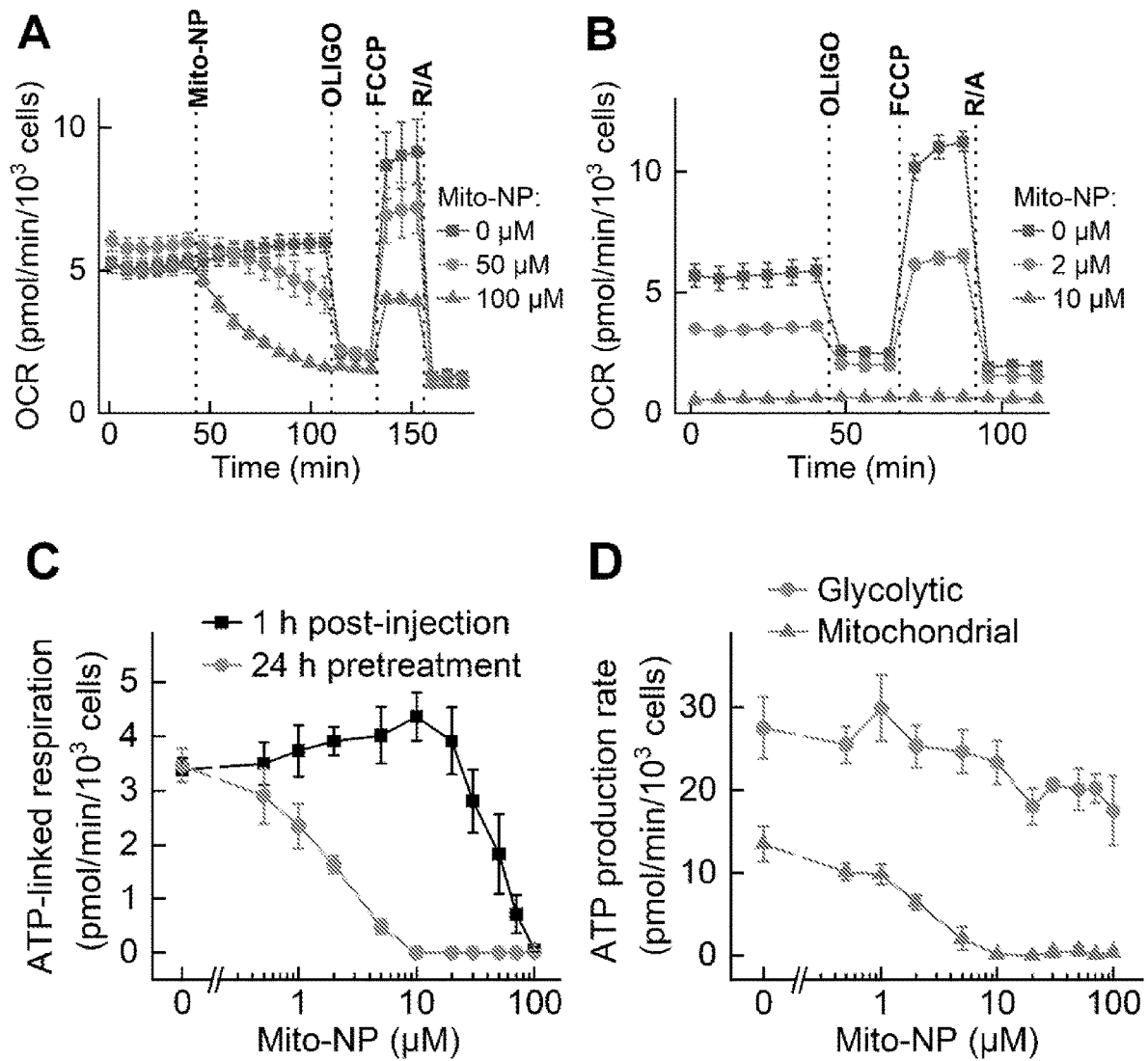
FIG. 16. Inhibition of mitochondrial respiration by Mito-NP in MiaPaCa2 cells. (A) Mito-NP injected during the measurements. (B) Cells pretreated with Mito-NP for 24 h. (C) Effect of Mito-NP concentration on ATP-linked respiration rate after 1 h and 24 h incubation. (D) Effect of Mito-NP concentration on glycolytic and mitochondrial ATP production rates after 24-h incubation.

Effects of Mito-NP on cellular bioenergetic function were studies using the Seahorse XF96 flux analyzer.[9,89] Addition of Mito-NP to MiaPaCa2 cells led to time- and concentration-dependent inhibition of mitochondrial respiration, and a loss of response to mitochondrial stressors, including oligomycin (complex V inhibitor), FCCP (mitochondrial uncoupler) and rotenone/antimycin A mix (inhibitors of mitochondrial complexes I and III) (FIG. 16). Immediately (1 h) after injection, a high concentration of Mito-NP (100 μM) was needed to block ATP-linked respiration (FIG. 16A,C). However, 24-h incubation led to a complete inhibition of ATP-linked respiration at 10 μM Mito-NP (FIG. 16B,C). One of the hallmarks of cancer cells is their flexibility in using different energetic substrates to sustain growth in the presence of metabolism-targeted drugs. However, while treatment with Mito-NP led to a decrease in the rate of mitochondrial ATP production (FIG. 16D), glycolytic ATP production remained unchanged at Mito-NP concentrations up to 10 μM and decreased at higher concentrations (FIG. 16D). This suggests that the redox stress induced by Mito-NP prevents cancer cells from compensatory activation of the glycolytic pathway.

Figure 10:
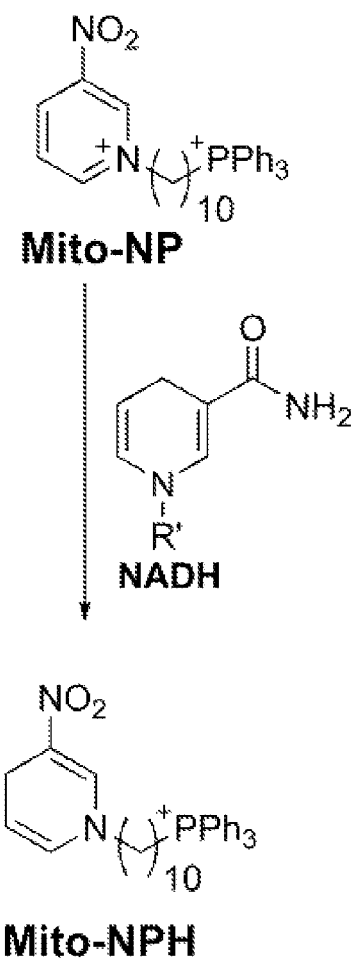
FIG. 10. Representative schematic of method of making a prodrug of the present invention.
Figure 11:
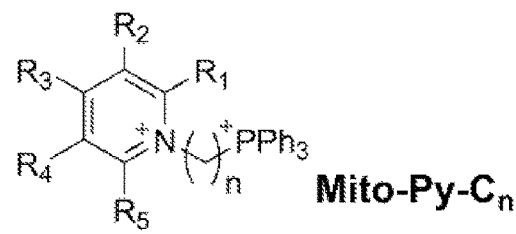
FIG. 11. Representative schematic of method of making prodrug of present invention.
Figure 11:
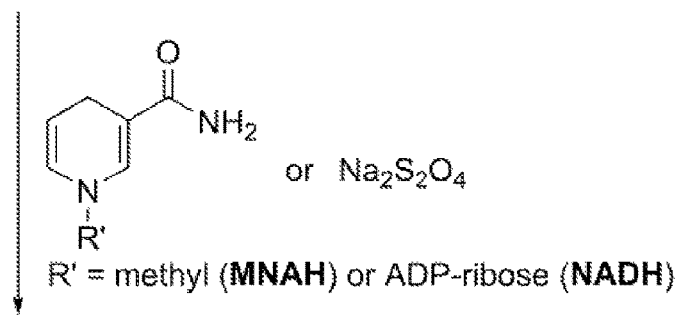
Figure 11:
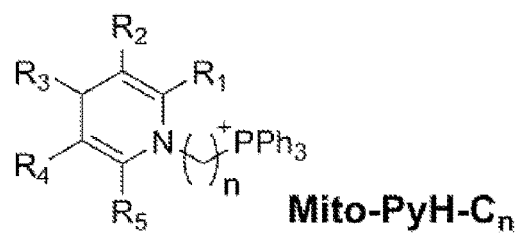
Figure 12:
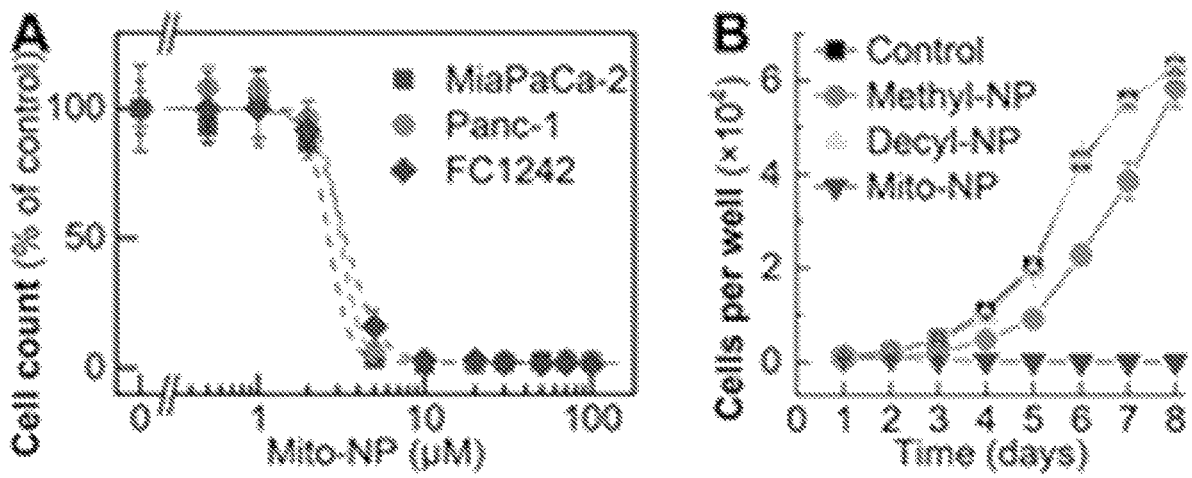
FIG. 12. (A) Antiproliferative potency of Mito-NP against different pancreatic cancer cells. (B) Comparison of the antiproliferative effects of Mito-NP, with its untargeted analogs (10 μM each).
Figure 17:
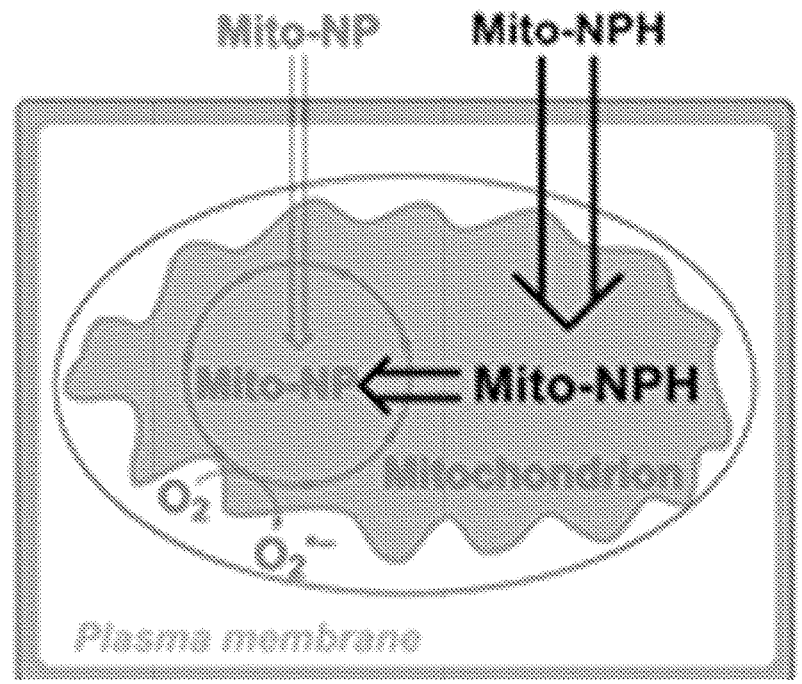
FIG. 17. Strategy to increase cell and tissue Mito-NP level by delivery of its more lipophilic dihydro-precursor, Mito-NPH.

4. Delivery of Mito-NP to cancer cells. One of the limitations of the mitochondria-targeted cationic agents is a slow transport through membranes, due to a high energy barrier for passing the lipid bilayer by multicharged compounds.[146] To improve the delivery of Mito-NP to the tumor tissue, we designed a strategy involving the delivery of more lipophilic, reduced precursor of Mito-NP (Mito-NPH), which has only a single positive charge of the lipophilic $TPP^+$ moiety. Two methods of synthesizing such prodrugs are shown in FIG. 10 and FIG. 11. We reasoned that Mito-NPH would accumulate in cells and tissues and undergo intracellular reoxidation, effectively increasing the cellular/tissue level of Mito-NP (FIG. 17).

Figure 18:
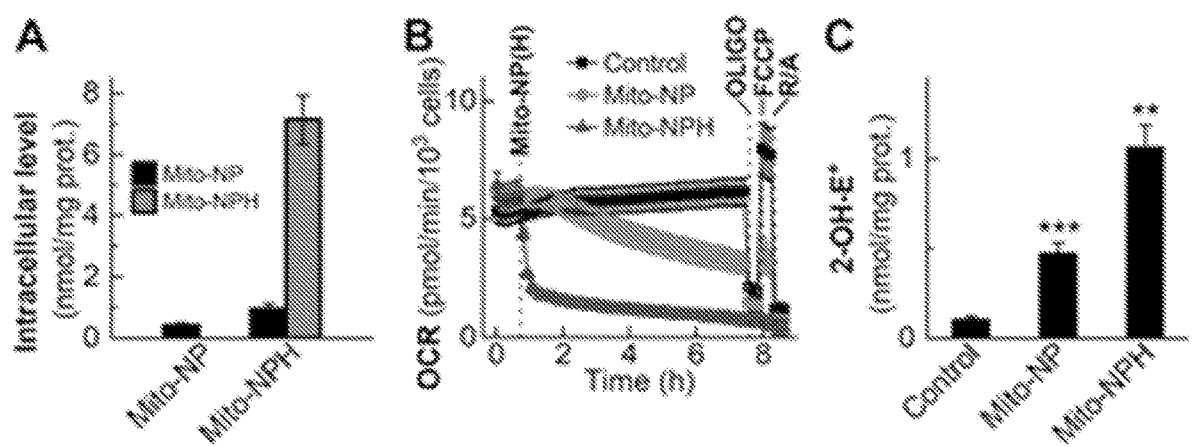
FIG. 18. (A) Intracellular level of Mito-NP and Mito-NPH. (B) Dynamics of inhibition of mitochondrial respiration by Mito-NP and Mito-NPH. (C) Intracellular generation. 10 μM Mito-NP or Mito-NPH was used.
Figure 19:
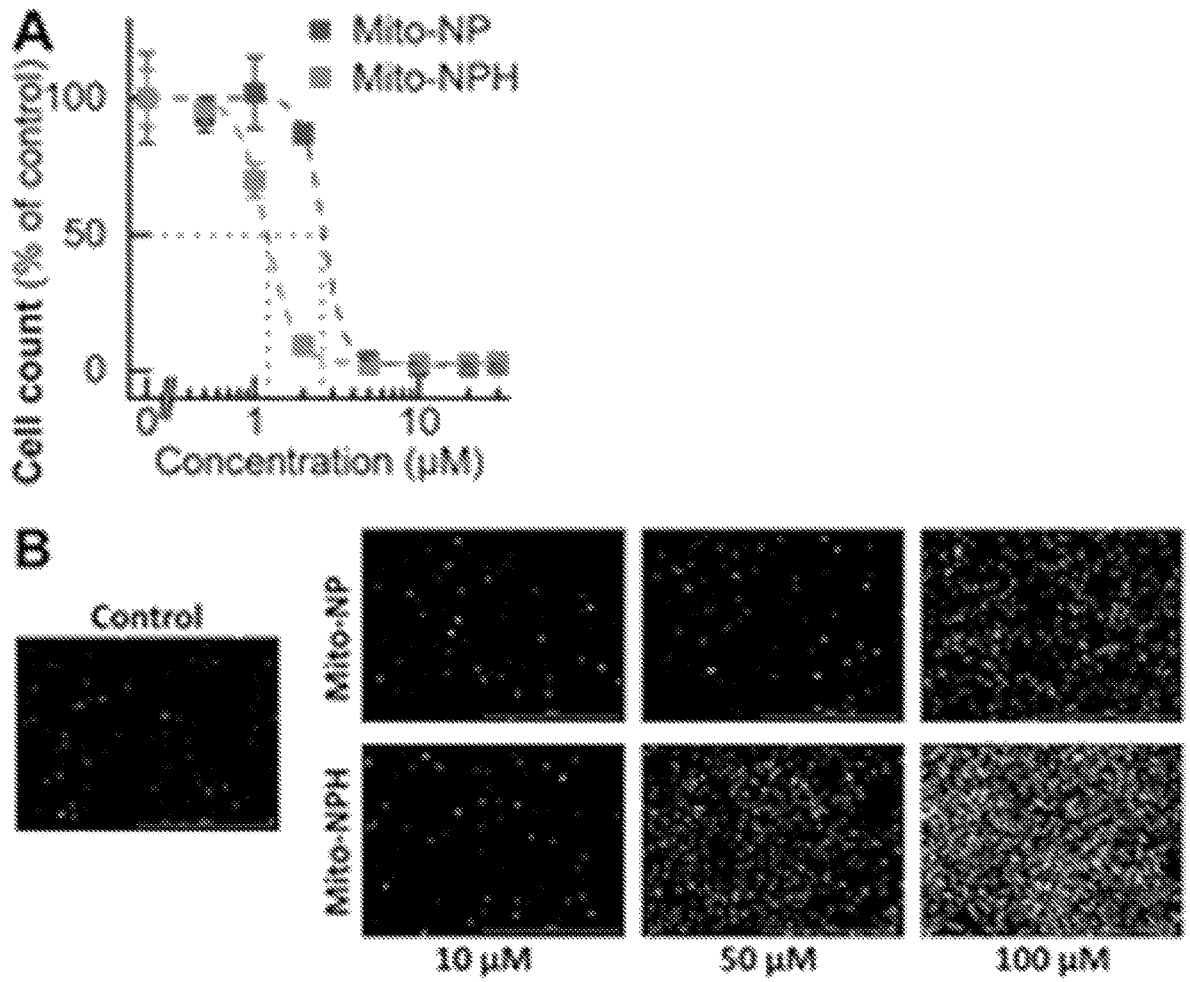
FIG. 19. Antiproliferative (A) and cytotoxic (B) potency of Mito-NP vs. Mito-NPH. MiaPaCa2 cells were incubated with the compounds for 5 days and cells counted (A) or for 24 h, followed by labeling with Sytox Green dead cell fluorescent stain (B).
Figure 20:
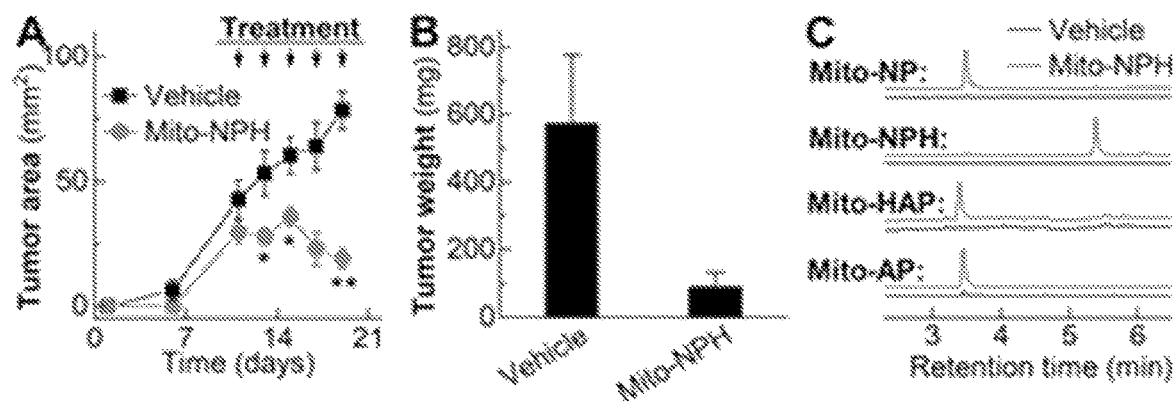
FIG. 20. In vivo effects of Mito-NPH on the FC1242 PDAC tumor growth in mice. (A) Tumor growth curves; (B) tumor wet weight after 9 days of treatment; and (C) LC-MS/MS traces of Mito-NP, Mito-NPH, and their metabolites: hydroxylamine (Mito-HAP) and amine (Mito-AP) derivatives extracted from tumor. n=5 per group, *p<0.05

We treated pancreatic cancer cells with Mito-NP or Mito-NPH and the intracellular levels of both oxidized, redox-cycling capable Mito-NP, and its cell membrane-permeable reduced precursor, Mito-NPH, were measured using LC-MS/MS. Treatment of MiaPaCa2 cells with Mito-NPH for 4 h led to 20-fold increase in total compound's uptake, with two-fold increase in the level of the redox-active oxidized form, Mito-NP (FIG. 18A). The dynamics of inhibition of mitochondrial respiration by Mito-NPH and Mito-NP was used to follow the compounds' uptake rates. More efficient inhibition of mitochondrial respiration by Mito-NPH (FIG. 18B) supports the conclusion of a lower energy barrier for the transfer though lipid bilayers and, thus faster cellular uptake and OXPHOS inhibition. The increased intracellular level of Mito-NP upon treatment with Mito-NPH also translated into 2-fold stronger stimulation of intracellular $O_2.^-$ production, as measured by monitoring $O_2.^-$-specific product of hydroethidine oxidation, 2-OH-$E^+$ (FIG. 18C). These data support the approach of cellular delivery of the reduced form of Mito-NP to increase its accumulation and improve the efficiency and potency. Next, we tested the effects of Mito-NPH on MiaPaCa2 cell proliferation and survival. As shown in FIG. 19, Mito-NPH is a more potent antiproliferative agent ($IC_{50}$=1.2±0.1 μM, FIG. 19A) and a significantly stronger cytotoxic agent, as measured with Sytox Green fluorescent stain (FIG. 19B). Therefore, increased uptake leads to more potent inhibition of mitochondrial function and stronger stimulation of $O_2.^-$ production, resulting in improved antiproliferative activity and increased cytotoxicity in pancreatic cancer cells. 5. Syngraft mouse model. We have established a preliminary syngraft model using mouse FC1242 PDAC cell line. After the tumor has been established and detectable by palpation (seven days after injection of tumor cells), Mito-NPH (0.2 mg per injection) was administered three times per week. Tumor size was measured using calipers and by weighing the tumor tissues at the completion of the study. Administration of Mito-NPH led to inhibition of the tumor growth (FIG. 20A,B). The tumor tissues were analyzed for the level of Mito-NP and Mito-NPH 24 h after the last injection of Mito-NPH. We detected both Mito-NP and Mito-NPH, as well as the product of reduction of the nitro group (FIG. 20C). These data demonstrate that Mito-NPH inhibits tumor growth in vivo.

Each publication, patent, and patent publication cited in this disclosure is incorporated in reference herein in its entirety. The present invention is not intended to be limited to the foregoing examples, but encompasses all such modifications and variations as come within the scope of the appended claims.

The invention claimed is:

1. A compound, which is of formula I or a prodrug thereof:

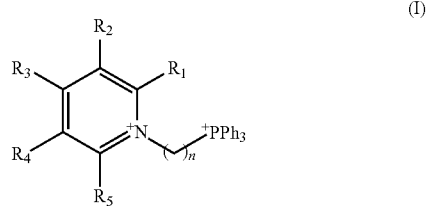

wherein
n is an integer selected from 1-18,
$R_1$, $R_2$, $R_3$, $R_4$ and $R_5$ are independently selected from —H, —$OCH_3$, —$CH_3$, —$CF_3$, —C(O)$NH_2$, —CN, —C(O)$CH_3$, and —$NO_2$,

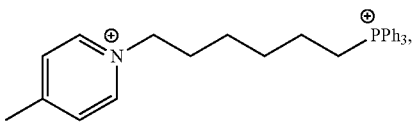

provide that the compound is not and provided that, where $R_2$ is —C(O)$NH_2$ and $R_1$, $R_3$, $R_4$ and $R_5$ are —H, then n is an integer 0 selected from 5-18.

2. The compound of claim 1, wherein n is an integer from 4-10, provided that, where $R_2$ is —C(O)NH$_2$ and $R_1$, $R_3$, $R_4$ and $R_5$ are —H, then n is an integer selected from 5-10.

3. The compound of claim 1, wherein $R_2$ is —CH$_3$, and $R_1$, $R_3$, $R_4$ and $R_5$ are —H.

4. The compound of claim 3, wherein the compound is Mito-MeP-C$_{10}$

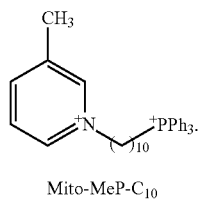

Mito-MeP-C$_{10}$

5. The compound of claim 1, wherein $R_2$ is —C(O)NH$_2$, $R_1$, $R_3$, $R_4$ and $R_5$ are —H, and n is an integer selected from 5-18.

6. The compound of claim 5, wherein the compound is Mito-NA-C$_{10}$.

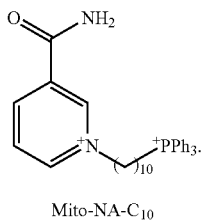

Mito-NA-C$_{10}$

7. The compound of claim 1, wherein $R_2$ is —CN and $R_1$, $R_3$, $R_4$ and $R_5$ are —H.

8. The compound of claim 7, wherein the compound is Mito-CNP-C$_{10}$

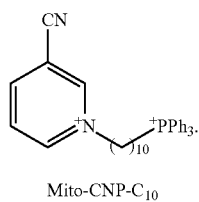

Mito-CNP-C$_{10}$

9. The compound of claim 1, wherein $R_2$ is —NO$_2$ and $R_1$, $R_3$, $R_4$ and $R_5$ are —H.

10. The compound of claim 9, wherein n is 4, 6, 8 or 10.

11. The compound of claim 10, wherein the compound is Mito-NP-C$_4$, Mito-NP-C$_6$, Mito-NP-C$_8$, or Mito-NP-C$_{10}$:

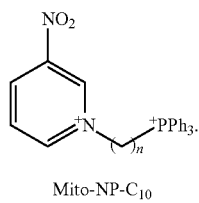

Mito-NP-C$_{10}$ n = 4, 6, 8, 10

12. The compound of claim 1, wherein the compound is a prodrug.

13. The compound of claim 1, wherein the compound is a prodrug of formula:

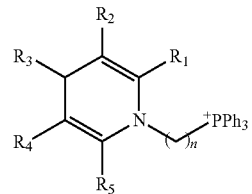

wherein $R_1$, $R_2$, $R_3$, $R_4$ and $R_5$, and n are as defined in claim 1.

14. The compound of claim 12, wherein the prodrug is:

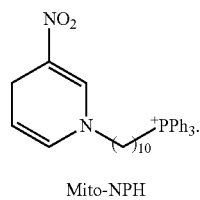

Mito-NPH

15. A method of stimulating superoxide production within a cell, the method comprising:
   contacting the cancer cell with the compound of claim 1 in an amount effective to inhibit cancer cell growth or proliferation.

16. The method of claim 15, wherein the cell is a colon cancer cell or pancreatic cancer cell.

17. The method of claim 15, wherein the cell is a drug-resistant cancer cell.

18. A method of inhibiting cancer cell growth or proliferation, the method comprising
   contacting the cancer cell with the compound of claim 1 in an amount effective to inhibit cancer cell growth or proliferation.

19. The method of claim 18, wherein the cancer cell is a cancer selected from the group consisting of colon cancer, rectum cancer, pancreas cancer, prostate cancer, lung and bronchus cancer, breast cancer, brain cancer, liver cancer, oral cancer, bladder cancer, stomach cancer, and leukemia.

20. The method of claim 19, wherein the cancer is drug resistant cancer.

21. The method of claim 18, wherein the cancer cell is in a subject and wherein the contacting comprises administering an effective amount of the compound to the subject.

22. The method of claim 21, wherein the method further comprises:
   administering radiation or chemotherapy in combination with the compound.

23. A method of treating cancer in a subject, the method comprising:
   administering a therapeutically effective amount of the compound of claim 1 in order to treat the cancer.

24. The method of claim 23, wherein the cancer is drug resistant cancer.

25. The method of claim 23, wherein the cancer cell is a cancer selected from the group consisting of colon cancer, rectum cancer, pancreas cancer, prostate cancer, lung and bronchus cancer, breast cancer, brain cancer, liver cancer, oral cancer, bladder cancer, stomach cancer, and leukemia.

26. The method of claim 23, wherein the method further comprises:
   administering the subject cancer treatment selected from radiation, chemotherapy, immunotherapy and combinations thereof.

27. The compound of claim 1, wherein $R_2$ is —C(O)NH$_2$, $R_1$, $R_3$, $R_4$ and $R_5$ are —H, and n is an integer selected from 8-18.

* * * * *